United States Patent
Merlette et al.

(10) Patent No.: US 6,398,818 B1
(45) Date of Patent: Jun. 4, 2002

(54) LOWER LEG PROSTHESIS

(75) Inventors: John B. Merlette, Wilson, WY (US); Eric W. Rubie, Salt Lake City; David J. Wall, Sandy, both of UT (US); James R. Brueggemann, Los Angeles, CA (US)

(73) Assignee: CRP, Inc., Salt Lake City, UT (US)

( * ) Notice: Subject to any disclaimer, the term of this patent is extended or adjusted under 35 U.S.C. 154(b) by 0 days.

(21) Appl. No.: 09/347,445

(22) Filed: Jul. 2, 1999

(51) Int. Cl.[7] ................................................. A61F 2/66
(52) U.S. Cl. ........................................ 623/55; 623/53
(58) Field of Search .............................. 623/55, 53, 52, 623/27, 28, 47, 49

(56) References Cited

U.S. PATENT DOCUMENTS

| | | | | |
|---|---|---|---|---|
| 546,405 A | * | 9/1895 | Marks et al. | 623/55 |
| 3,766,569 A | * | 10/1973 | Orange | 623/55 |
| 4,225,982 A | * | 10/1980 | Cochrane et al. | 623/55 |
| 4,822,363 A | * | 4/1989 | Phillips | 623/27 |
| 4,959,073 A | * | 9/1990 | Merlette | 623/55 |
| 5,062,859 A | * | 11/1991 | Naeder | 623/55 |
| 5,156,631 A | | 10/1992 | Merlette | 623/52 |
| 5,258,039 A | * | 11/1993 | Goh et al. | 623/55 |
| 5,769,896 A | * | 6/1998 | Rosendahl et al. | 623/49 |
| 5,800,569 A | * | 9/1998 | Phillips | 623/55 X |
| 6,099,572 A | * | 8/2000 | Mosler et al. | 623/53 |

\* cited by examiner

Primary Examiner—Corrine McDermott
Assistant Examiner—Brian E. Pellegrino
(74) Attorney, Agent, or Firm—Sheppard, Mullin, Richter & Hampton LLP; James R. Brueggemann

(57) ABSTRACT

An improved lower leg prosthesis is disclosed that, during use, provides an improved dynamic feel at heel strike and that provides improved inversion/eversion compliance. The prosthesis includes an elongated pylon having an upper, generally vertical section and a lower, forwardly oriented foot section, and it further includes a generally horizontally oriented foot plate disposed beneath the pylon and including a heel section projecting a substantial distance rearwardly of a vertical pylon axis. An elastomeric layer is interposed between the pylon and the foot plate, extending along substantially the entire length of the heel section of the foot plate, for attaching the pylon and foot plate together. During use of the prosthesis, at heel strike, upward deflection of the foot plate's heel section is limited in substantial part both by the stiffness of the heel section, itself, and by compression of the portion of the elastomeric layer disposed rearwardly of the vertical pylon axis.

20 Claims, 3 Drawing Sheets

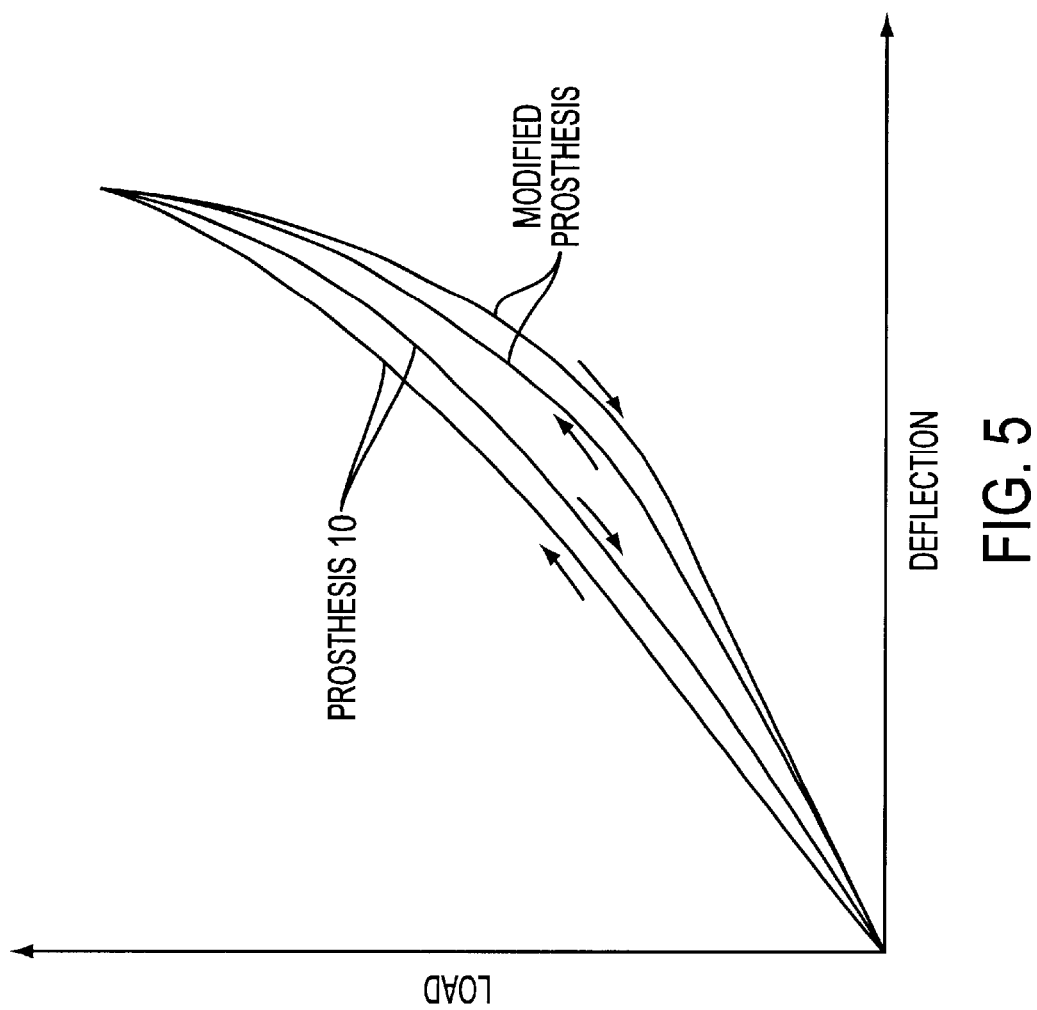

LOWER LEG PROSTHESIS

BACKGROUND OF THE INVENTION

This invention relates generally to lower leg prostheses and, more particularly, to lower leg prostheses configured to duplicate the dynamic performance characteristics of the human foot and ankle.

Significant advancements in the field of lower leg prostheses have been made in recent years, due largely to the development of composite materials technology. Lower leg prostheses incorporating fiberglass/epoxy and carbon fiber/epoxy composite materials have been developed, which closely duplicate the dynamic performance characteristics of the human foot and ankle.

One such lower leg prosthesis is disclosed in U.S. Pat. No. 4,959,073 issued to Merlette. The Merlette prosthesis incorporates an elongated composite main member having a leg section and a forwardly extending foot section, and it further incorporates a heel member projecting rearwardly from the underside of the main member's foot section. A high-density polyurethane elastomer is disposed between the heel member and the main member's foot section, to permanently attach the two members together and to provide limited cushioning. The upper end of the main member's leg section supports an amputation socket for receiving the amputee's residual limb, and a crepe sole can be attached to the underside of the heel member. A foam foot shell or cosmesis can be placed over the composite members, to provide the prosthesis with an appearance of a natural human foot.

The Merlette lower leg prosthesis described briefly above has enjoyed substantial commercial success. Nevertheless, it is believed that the Merlette prosthesis can be improved upon by modifying the structure that resists upward deflection of its heel section at heel strike and also by providing enhanced inversion/eversion compliance.

It should therefore be appreciated that there exists a need for a lower leg prosthesis that, during use, provides an improved dynamic feel at heel strike and that provides improved inversion/eversion compliance. The present invention fulfills this need and provides further related advantages.

SUMMARY OF THE INVENTION

The present invention is embodied in an improved lower leg prosthesis that, during use, provides an improved dynamic feel at heel strike and that provides improved inversion/eversion compliance. The prosthesis includes an elongated pylon having an upper, generally vertical section and a lower, forwardly oriented foot section, wherein the upper section defines a vertical pylon axis, and it further includes a generally horizontally oriented foot plate disposed beneath the pylon and including a heel section projecting a substantial distance rearwardly of the vertical pylon axis. The pylon and the foot plate both are formed of a high-strength composite material, e.g., an epoxy/carbon fiber composite material. Further, an elastomeric layer, e.g., formed of a high-density polyurethane material, is interposed between the pylon and the foot plate, extending along substantially the entire length of the heel section of the foot plate, for attaching the pylon and foot plate together. During use of the prosthesis, at heel strike, upward deflection of the foot plate's heel section is limited in substantial part both by the stiffness of the heel section, itself, and by compression of the portion of the elastomeric layer disposed rearwardly of the vertical pylon axis.

In a more detailed feature of the invention, the forward tip of the foot plate is disposed substantially beneath the forward tip of the pylon's forwardly oriented foot section, and the elastomeric layer extends along substantially the entire length of the foot plate, from its forward tip to the rearward tip. The elastomeric layer preferably has a width that tapers from a minimum at the foot plate's forward tip to a maximum at a mid-portion of the foot plate to a minimum at the foot plate's rearward tip. In addition, the pylon's forwardly oriented foot section has a width that tapers from a maximum at a location substantially aligned with the maximum width of the elastomeric layer to a minimum at the foot section's forward tip. The points of maximum width of the pylon's forwardly oriented foot section and the elastomeric layer preferably are located forward of the vertical pylon axis.

In other more detailed features of the invention, the portion of the elastomeric layer disposed on the heel section of the foot plate has a concave upper surface. This concave upper surface preferably is a circular arc, substantially tangent both to the pylon's upper, vertical section and to the foot plate's rearward tip.

The portion of the elastomeric layer disposed rearwardly of the vertical pylon axis preferably provides at least about one-third of the total resistance to upward flexing of the foot plate's heel section at heel strike. In addition, this layer has a thickness of at least about one-half centimeter along substantially its entire length.

Other features and advantages of the present invention should become apparent from the following description of the preferred embodiments, taken in conjunction with the exemplary drawings, which illustrate the principles of the invention.

BRIEF DESCRIPTION OF THE DRAWINGS

FIG. 5 is a graph depicting the heel tip deflection as a function of load, both for the lower leg prosthesis of FIG. 1 and for a similar prosthesis in which the portion of the elastomeric layer disposed rearwardly of the vertical pylon axis has been removed, normalized to have the same total deflection at maximum load.

DESCRIPTION OF THE PREFERRED EMBODIMENT

Figure 1:
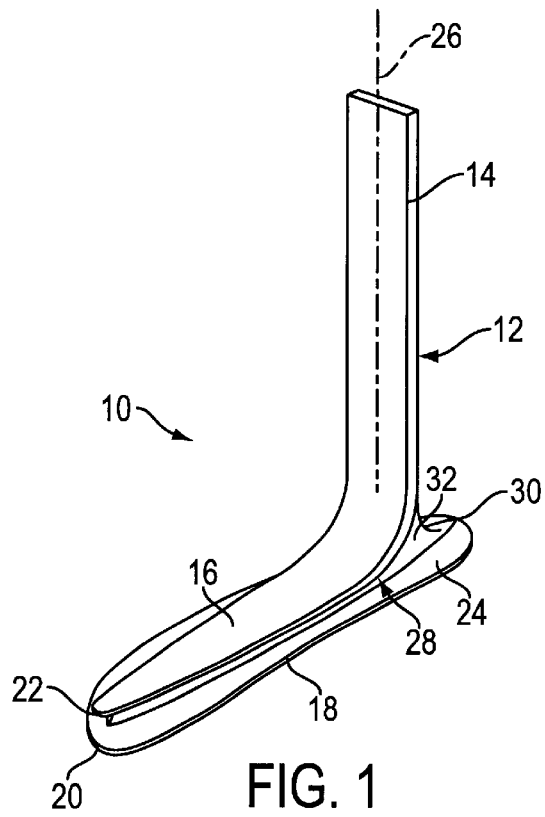
FIG. 1 is a perspective view of a lower leg prosthesis in accordance with the invention, the prosthesis including a pylon and a foot plate that are permanently attached to each other by an intermediate elastomeric layer.
Figure 4:
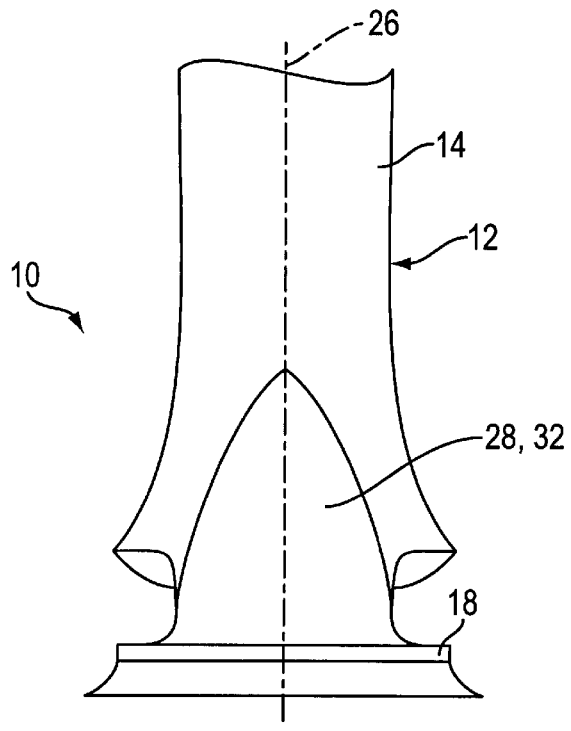
FIG. 4 is a rear elevational view of the lower leg prosthesis of FIG. 1.
Figure 2:
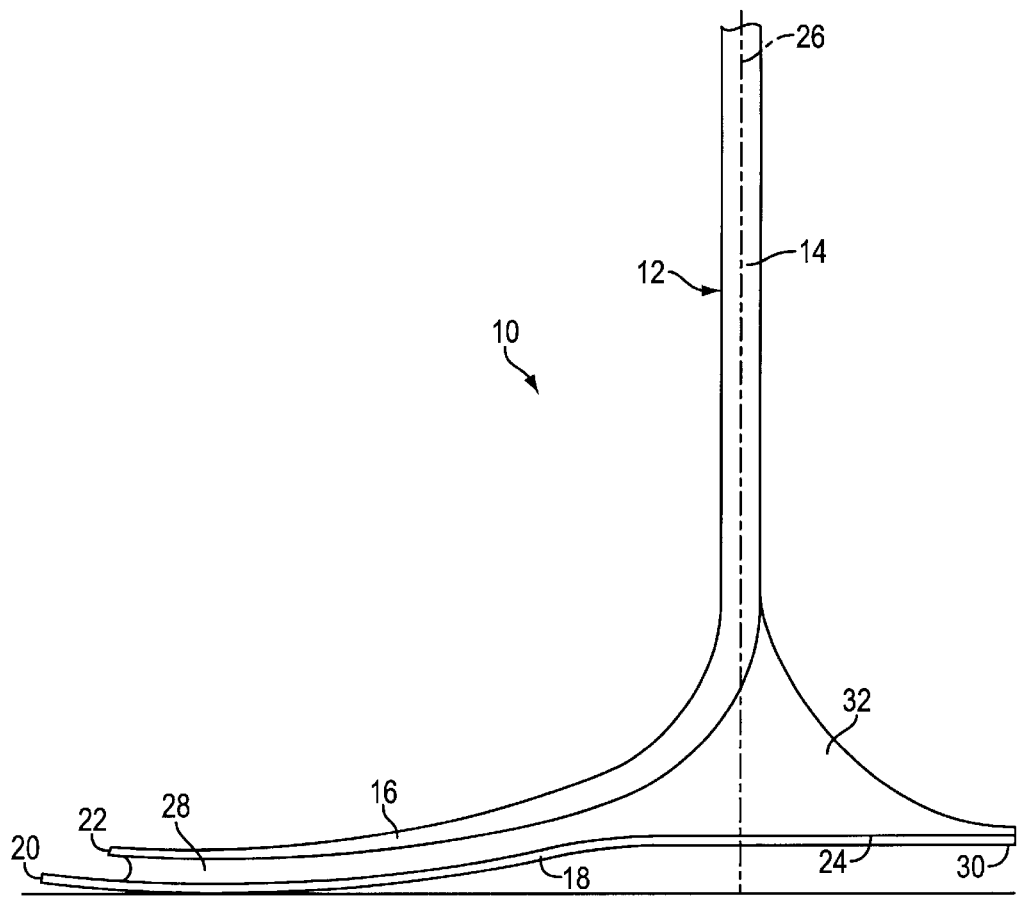
FIG. 2 is a side elevational view of the lower leg prosthesis of FIG. 1.

With reference now to the illustrative drawings, and particularly to FIGS. 1–4, there is shown a lower leg prosthesis 10 in accordance with the invention, the prosthesis incorporating an elongated pylon 12 having an upper, vertically oriented ankle/shin section 14 and a lower, forwardly oriented forefoot section 16, and further incorporating an underlying foot plate 18. As best shown in FIG. 2, the forward tip 20 of the foot plate is disposed substantially beneath the forward tip 22 of the pylon's forefoot section. In addition, the foot plate's rearward end defines a heel section 24 that projects rearwardly of a vertical axis 26 defined by the pylon's ankle/shin section. An elastomeric layer 28 extends along substantially the entire length of the foot plate, for permanently attaching the foot plate to the pylon. The prosthesis duplicates the dynamic performance characteristics of the normal human foot, yet it is of simple construction and can be manufactured relatively inexpensively.

The pylon 12 preferably is formed of a conventional epoxy/carbon fiber material, and it has a rectangular cross-section along its entire length. The pylon's ankle/shin section 14 transitions smoothly downwardly and forwardly to the forefoot section 16. The pylon's width is substantially uniform along the ankle/shin section, but increases to a maximum at the beginning of the forefoot section and then tapers to a minimum at the forefoot section's forward tip 22. The pylon's thickness, likewise, is substantially uniform along the ankle/shin section, but increases to a maximum where it transitions to the forefoot section, and then decreases through the forefoot section to a minimum thickness at the forward tip.

Figure 3:
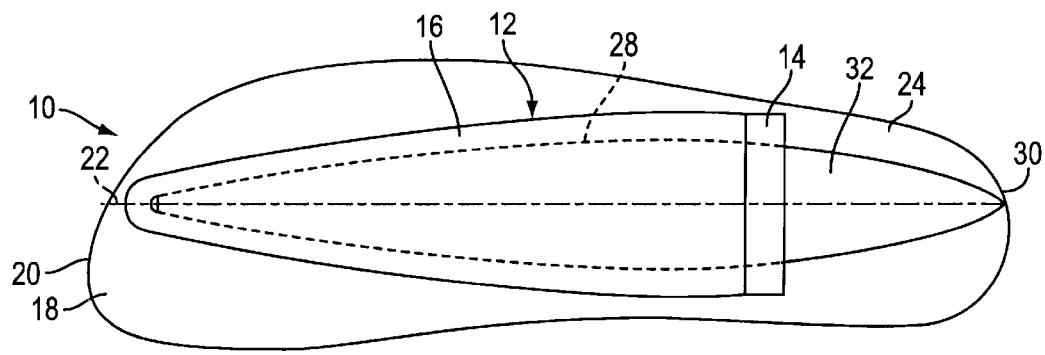
FIG. 3 is a top plan view of the lower leg prosthesis of FIG. 1.

The foot plate 18, likewise, preferably is formed of a conventional epoxy/carbon fiber material, and it has a rectangular cross-section along its entire length. The foot plate's peripheral shape generally matches that of a natural human foot, as best shown in FIG. 3. In addition, the foot plate's thickness is generally uniform, but tapers to minimum at the foot plate's toe tip 20 and heel tip 30.

The elastomeric layer 28 is formed of a high-density polyurethane material, and it is interposed between the foot plate 18 and the forefoot section 16 of the pylon 12 to permanently bond the members together. This elastomeric layer extends along substantially the entire length of the foot plate, from its toe tip 22 to its heel tip 30. In the region beneath the forefoot section, the elastomeric layer has a substantially uniform thickness of about one-half centimeter and a width that is slightly narrower than that of the forefoot section, thus tapering to a minimum at its forward tip.

The portion of the elastomeric layer 28 that is disposed rearwardly of the pylon's vertical axis 26, which portion is identified by the reference numeral 32, interconnects the foot plate's heel section 24 to the portion of the pylon 12 that transitions between its ankle/shin section 14 and forefoot section 16. The width of this elastomeric layer portion 32 tapers smoothly to a minimum at the heel tip 30. In addition, the thickness of this elastomeric layer portion has a concave curvature, with a substantially uniform radius of about six centimeters. This curvature has tangent points substantially at the heel tip 30 and at the ankle/shin section 14. It will be appreciated that alternative shapes for this elastomeric layer portion 32 also could be used.

The elastomeric layer portion 32 disposed rearwardly of the pylon's vertical axis 26 functions not only to assist in permanently attaching the foot plate 18 to the pylon 12, but also to enhance the performance of the prosthesis 10 during its use, particularly at heel strike. During the heel strike phase of the amputee's gait, the heel section 24 of the foot plate 18 deflects upwardly, to cushion the prosthesis' impact on the ground. Resistance to this upward deflection is provided not only by the inherent stiffness of the heel section, itself, but also by compression of the elastomeric layer portion 32. This contrasts with many prior composite lower leg prostheses incorporating projecting heel sections, which resist upward deflection of the heel section solely by the heel section's inherent stiffness.

At the point of maximum deflection, the compression of the elastomeric layer portion 32 is believed to contribute about one-third of the prosthesis' total resistance to deflection of the heel section 24 of the foot plate 18. Thus, if a prosthesis were to be constructed without the elastomeric layer portion, a similar amount of upward deflection of the heel section would occur for an impact force about one-third less in magnitude.

Moreover, the inherent stiffness of the heel section 24 of the foot plate 18 and compression of the elastomeric layer portion 32 contribute in different ways to resisting upward deflection of the heel section. In particular, the contribution of the elastomeric layer portion to upward deflection tends to be greatest when impact forces are low, while the contribution of the inherent stiffness of the heel section tends to be greatest when impact forces are high.

The different dynamic performance characteristics of the heel section 24 and the elastomeric layer portion 32 in resisting the heel section's upward deflection can be appreciated with reference to FIG. 5, which depicts a graph of the heel section's load/deflection curve. Actually, two curves for the load/deflection relationship are presented, including one showing the deflection as the load is being applied and the other showing the deflection as the load is being removed. Slightly greater deflection occurs in the latter case, for a given load.

Also depicted in FIG. 5 is a graph of the load/deflection curves for a prosthesis constructed without an elastomeric layer portion located rearwardly of the prosthesis' vertical pylon axis, normalized to have a total deflection the same as that of the prosthesis 10. It will be noted that the prosthesis 10 experiences less deflection of its heel section at non-maximum loads. This difference is believed to provide an improved dynamic feel for the amputee.

Another performance benefit provided by the elastomeric layer 28 results from its substantial thickness along its entire length. As mentioned above, the layer has a substantially uniform thickness of about one-half centimeter along its entire length beneath the pylon's forefoot section 16. This thickness facilitates limited articulation, including inversion and eversion movement, of the pylon 12 relative to the foot plate 18. The prosthesis 10 thereby better duplicates the motion of the natural human foot.

It should be appreciated from the foregoing description that the present invention provides an improved lower leg prosthesis that, during use, provides an improved dynamic feel at heel strike and that provides improved inversion/eversion compliance. The prosthesis includes an elongated pylon having an upper, generally vertical section and a lower, forwardly oriented foot section, and it further includes a generally horizontally oriented foot plate disposed beneath the pylon and including a heel section projecting a substantial distance rearwardly of a vertical pylon axis. An elastomeric layer is interposed between the pylon and the foot plate, extending along substantially the entire length of the heel section of the foot plate, for attaching the pylon and foot plate together. During use of the prosthesis, at heel strike, upward deflection of the foot plate's heel section is limited in substantial part both by the stiffness of the heel section, itself, and by compression of the portion of the elastomeric layer disposed rearwardly of the vertical pylon axis.

Although the invention has been described in detail with reference to the presently preferred embodiment, those of ordinary skill in the art will appreciate that various modifications can be made without departing from the invention. Accordingly, the invention is defined only by the following claims.

I claim:

1. A lower leg prosthesis comprising:
   an elongated pylon having an upper, generally vertical section and a lower, forwardly oriented forefoot section, wherein the upper section defines a vertical pylon axis;

a generally horizontally oriented foot plate disposed beneath the pylon and including a heel section projecting a substantial distance rearwardly of the vertical pylon axis;

wherein the pylon and the foot plate both are formed of a high-strength composite material; and an elastomeric layer interposed between, and attaching together, the pylon and the foot plate, wherein the elastomeric layer extends to substantially the rearwardmost end of the heel section of the foot plate and along substantially the entire length of the foot plate, but does not extend beneath the foot plate or atop the forefoot section of the pylon;

wherein during use of the prosthesis, at heel strike, upward deflection of the heel section of the foot plate is limited in substantial part both by the stiffness of the heel section, itself, and by compression of the portion of the elastomeric layer disposed rearwardly of the vertical pylon axis.

2. A lower leg prosthesis as defined in claim 1, wherein:
the forefoot section of the pylon terminates at a forward tip:
the foot plate extends from a forward tip to a rearward tip;
the forward tip of the foot plate is disposed substantially beneath the forward tip of the pylon's forefoot section; and
the elastomeric layer extends along substantially the entire length of the foot plate, from its forward tip to its rearward tip.

3. A lower leg prosthesis as defined in claim 2, wherein the elastomeric layer has a width that tapers from a minimum at the foot plate's forward tip to a maximum at a mid-portion of the foot plate to a minimum at the foot plate's rearward tip.

4. A lower leg prosthesis as defined in claim 3, wherein the pylon's forefoot section has a width that tapers from a maximum at a location substantially aligned with the maximum width of the elastomeric layer to a minimum at the forefoot section's forward tip.

5. A lower leg prosthesis as defined in claim 4, wherein the points of maximum width of the pylon's forefoot section and the elastomeric layer are located forward of the vertical pylon axis.

6. A lower leg prosthesis as defined in claim 2, wherein the portion of the elastomeric layer disposed on the heel section of the foot plate has a concave upper surface.

7. A lower leg prosthesis as defined in claim 6, wherein the concave upper surface of the portion of the elastomeric layer disposed on the heel section of the foot plate is a circular arc, substantially tangent both to the pylon's upper, vertical section and to the foot plate's rearward tip.

8. A lower leg prosthesis as defined in claim 1, wherein the pylon and the foot plate each are of unitary construction.

9. A lower leg prosthesis as defined in claim 8, wherein:
the unitary pylon and the unitary foot plate each are formed of an epoxy/carbon fiber composite material;
the elastomeric layer is formed of a high-density polyurethane material; and
the elastomeric layer non-removably attaches the foot plate to the pylon.

10. A lower leg prosthesis as defined in claim 1, wherein the portion of the elastomeric layer disposed rearwardly of the vertical pylon axis provides at least about one-third of the total resistance to upward deflection of the foot plate's heel section at heel strike.

11. A lower leg prosthesis as defined in claim 1, wherein the elastomeric layer has a thickness of at least about one-half centimeter along substantially its entire length.

12. A lower leg prosthesis comprising:
an elongated pylon having an upper, generally vertical section and a lower, forwardly oriented forefoot section, wherein the upper section defines a vertical pylon axis;

a generally horizontally oriented foot plate disposed beneath the pylon and including a heel section projecting a substantial distance rearwardly of the vertical pylon is;

wherein the pylon and the foot plate both are formed of a high-strength composite material; and an elastomeric layer interposed between, and attaching together, the pylon and the foot plate, wherein the elastomeric layer extends to substantially the rearwardmost end of the heel section of the foot plate and along substantially the entire length of the foot plate, but does not extend beneath the foot plate or atop the forefoot section of the pylon;

wherein during use of the prosthesis, at heel strike, upward deflection of the heel section of the foot plate is limited in substantial part both by the stiffness of the heel section, itself, and by compression of the portion of the elastomeric layer disposed rearwardly of the vertical pylon axis, with such compression of the elastomeric layer providing at least about one-third of the total resistance to upward deflection.

13. A lower leg prosthesis as defined in claim 12, wherein:
the forefoot section of the pylon terminates at a forward tip;
the foot plate extends from a forward tip to a rearward tip;
the forward tip of the foot plate is disposed substantially beneath the forward tip of the pylon's forefoot section; and
the elastomeric layer extends along substantially the entire length of the foot plate, from its forward tip to the rearward tip.

14. A lower leg prosthesis as defined in claim 13, wherein the portion of the elastomeric layer disposed on the heel section of the foot plate has a concave upper surface.

15. A lower leg prosthesis as defined in claim 14, wherein the concave upper surface of the portion of the elastomeric layer disposed on the heel section of the foot plate is a circular arc, substantially tangent both to the pylon's upper, vertical section and to the foot plate's rearward tip.

16. A lower leg prosthesis as defined in claim 12, wherein the pylon and the foot plate each are of unitary construction.

17. A lower leg prosthesis as defined in claim 16, wherein:
the unitary pylon and the unitary foot plate each are formed of an epoxy/carbon fiber composite material;
the elastomeric layer is formed of a high-density polyurethane material; and
the elastomeric layer non-removably attaches the foot plate to the pylon.

18. A lower leg prosthesis as defined in claim 12, wherein the elastomeric layer has a thickness of at least about one-half centimeter along substantially its entire length.

19. A lower leg prosthesis as defined in claim 12, wherein the elastomeric layer is interposed between the pylon and the foot plate, but does not extend beneath the foot plate or atop the forefoot section of the pylon.

20. A lower leg prosthesis comprising:
an elongated pylon having an upper, generally vertical section and a lower, forwardly oriented forefoot section, wherein the upper section defines a vertical pylon axis, and wherein the forward end of the forefoot section defines a forward tip;

a generally horizontally oriented foot plate disposed beneath the pylon and including a heel section projecting a substantial distance rearwardly of the vertical pylon axis, wherein the foot plate extends from a forward tip to a rearward tip;

wherein the forward tip of the foot plate is disposed substantially beneath the forward tip of the pylon's forefoot section;

wherein the pylon and the foot plate both are of unitary construction and formed of an epoxy/carbon fiber composite material; and an elastomeric layer interposed between, and non-removably attaching together, the pylon and the foot plate, wherein the elastomeric layer extends to substantially the rearward tip of the foot plate and along substantially the entire length of the foot plate, but does not end beneath the foot plate or atop the forefoot section of the pylon, and wherein the elastomeric layer is a high-density polyurethane material and has a thickness of at least about one-half centimeter along substantially its entire length;

wherein during use of the prosthesis, at heel strike, upward deflection of the heel section of the foot plate is limited both by the stiffness of the heel section, itself, and by compression of the portion of the elastomeric layer disposed rearwardly of the vertical pylon axis, with such compression of the elastomeric layer providing at least about one-third of the total resistance to upward deflection.

* * * * *

UNITED STATES PATENT AND TRADEMARK OFFICE
CERTIFICATE OF CORRECTION

PATENT NO. : 6,398,818 B1  
DATED : June 4, 2002  
INVENTOR(S) : Merlette et al.

It is certified that error appears in the above-identified patent and that said Letters Patent is hereby corrected as shown below:

Column 6,  
Line 12, "is" should be -- axis --.

Column 8,  
Line 3, "end" should be -- extend --.

Signed and Sealed this

Fifth Day of August, 2003

JAMES E. ROGAN  
*Director of the United States Patent and Trademark Office*